(12) United States Patent
Wills et al.

(10) Patent No.: US 10,512,529 B2
(45) Date of Patent: Dec. 24, 2019

(54) USE OF RESONANT SYSTEMS TO AUTOMATICALLY MODIFY POWER (AMPLITUDE) OF AN ORAL CARE APPLIANCE UPON USE IN-MOUTH

(71) Applicant: KONINKLIJKE PHILIPS N.V., Eindhoven (NL)

(72) Inventors: Scott Robert Wills, Shoreline, WA (US); Meng Peng, Bothell, WA (US); Sungsoo Lee, Kirkland, WA (US)

(73) Assignee: Koninklijke Philips N.V., Eindhoven (NL)

( * ) Notice: Subject to any disclaimer, the term of this patent is extended or adjusted under 35 U.S.C. 154(b) by 298 days.

(21) Appl. No.: 15/525,140

(22) PCT Filed: Nov. 17, 2015

(86) PCT No.: PCT/IB2015/058858
§ 371 (c)(1),
(2) Date: May 8, 2017

(87) PCT Pub. No.: WO2016/079660
PCT Pub. Date: May 26, 2016

(65) Prior Publication Data
US 2018/0271630 A1    Sep. 27, 2018

Related U.S. Application Data

(60) Provisional application No. 62/082,881, filed on Nov. 21, 2014.

(51) Int. Cl.
*A61C 17/22* (2006.01)
*A61C 17/34* (2006.01)

(52) U.S. Cl.
CPC ............ *A61C 17/221* (2013.01); *A61C 17/34* (2013.01); *A61C 17/3418* (2013.01)

(58) Field of Classification Search
CPC .... A61C 17/221; A61C 17/3418; A61C 17/34
See application file for complete search history.

(56) References Cited

U.S. PATENT DOCUMENTS

| 5,189,751 A | * | 3/1993 | Giuliani | ................. | A61C 17/20 |
| | | | | | 15/22.1 |
| 5,453,644 A | * | 9/1995 | Yap | ........................ | A45D 20/30 |
| | | | | | 200/61.85 |

(Continued)

FOREIGN PATENT DOCUMENTS

| DE | 102004022663 A1 | 12/2005 |
| EP | 1193844 A1 | 4/2002 |
| GB | 899618 | 6/1962 |

*Primary Examiner* — Marc Carlson

(57) ABSTRACT

An oral care appliance (100), such as an electric toothbrush, utilizing non-linear resonant systems is described herein. In one exemplary embodiment, the oral care appliance includes a longitudinal shaft (102), a brush head (130), and a handle (190). The handle includes a motor (140) that generates a first amplitude (404) for the brush head based on the brush head being outside of the user's mouth, when no mass is applied to the brush head. In response to the brush head being inside of the user's mouth, when mass is applied, such as by pressing the brush head against the teeth, the motor causes a second amplitude (410) to be generated for the brush head that is larger than the first amplitude.

9 Claims, 8 Drawing Sheets

(56) References Cited

U.S. PATENT DOCUMENTS

| | | | | |
|---|---|---|---|---|
| 7,025,774 B2* | 4/2006 | Freeman | ............ | A61B 5/15178 |
| | | | | 606/181 |
| 7,175,642 B2* | 2/2007 | Briggs | ............... | A61B 5/14546 |
| | | | | 600/583 |
| 7,563,232 B2* | 7/2009 | Freeman | ............ | A61B 5/14546 |
| | | | | 600/583 |
| 9,190,881 B1* | 11/2015 | Jahani | ....................... | H02K 7/06 |
| 9,248,267 B2* | 2/2016 | Freeman | ............... | A61M 37/00 |
| 9,301,822 B2* | 4/2016 | Grez | ...................... | A61C 17/32 |
| 9,757,219 B2* | 9/2017 | Kleppen | ................ | A61C 17/34 |
| 2003/0000032 A1* | 1/2003 | Lev | ........................ | A61C 17/22 |
| | | | | 15/28 |
| 2006/0037197 A1 | 2/2006 | Hawes et al. | | |
| 2012/0202166 A1* | 8/2012 | Kilcher | ................... | A61C 1/07 |
| | | | | 433/27 |
| 2012/0246846 A1* | 10/2012 | Hall | ................... | A46B 15/0004 |
| | | | | 15/22.1 |

* cited by examiner

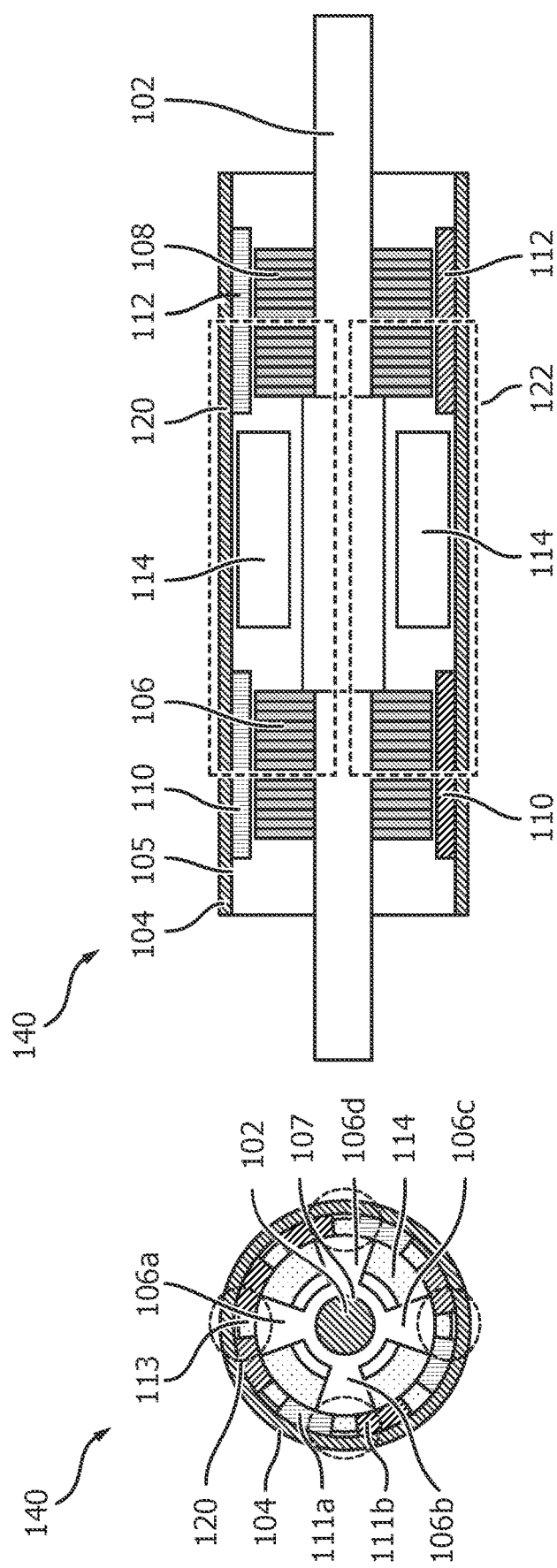

USE OF RESONANT SYSTEMS TO AUTOMATICALLY MODIFY POWER (AMPLITUDE) OF AN ORAL CARE APPLIANCE UPON USE IN-MOUTH

CROSS-REFERENCE TO PRIOR APPLICATIONS

This application is the U.S. National Phase application under 35 U.S.C. § 371 of International Application No. PCT/IB2015/058858, filed on Nov. 17, 2015, which claims the benefit of U.S. Provisional Patent Application No. 62/082,881, filed on Nov. 21, 2014. These applications are hereby incorporated by reference herein.

BACKGROUND OF THE INVENTION

1. Field of the Invention

The present invention generally relates to resonant electric oral care appliance and, in particular, non-linear resonant systems capable of modifying an amplitude of an electric oral care appliance, such as a toothbrush, based on whether the appliance is in a user's mouth or outside of the user's mouth.

2. Description of the Related Art

Electric toothbrushes and other electric oral care appliances have become increasingly popular for consumers as product costs have decreased while variety and effectiveness have skyrocketed. Most electric oral care appliances include a few general components. One component, such as a brush head, allows a user to clean teeth, tongue, and/or gums, in some cases by applying an oral hygiene product (e.g., toothpaste), using the brush head. The brush head commonly provides a direct interaction between the oral care appliance and the user's teeth, tongue, gums, and mouth. However, persons of ordinary skill in the art will recognize that although a brush head is described above, a variety of other oral hygiene components may be used including, but not limited to, a tongue cleaner, an electric flossing mechanism, such as an Airflosss™, or any other type of oral hygiene component, or any combination thereof. However, for simplicity, a brush head will be used to further describe the features of the present disclosure.

The brush head is typically attached to a longitudinal shaft that connects to a handle housing various electronics, systems, and controls. The handle may also include one or more drive or actuator elements that allow, in the case of resonant toothbrush systems, a vibration or pulse to be translated through the shaft to the brush head. These pulses or vibrations cause the brush head to move with an effective amplitude about a rotational axis or in a lateral direction. Non-electric toothbrushes, on the other hand, lack the ability to generate any amplitude at the brush head without a user directly providing such amplitude, thereby making the overall brushing experience less effective and enjoyable. Furthermore, electric oral care appliances may generate high frequency vibrations with effective amplitude ranges for brushes. Non-electric oral care appliances may reach the desired amplitude range, however the time to do so is often much slower Some electric toothbrushes, as described in commonly assigned U.S. Patent Application Publication No. 2012/0246846, which is incorporated herein by reference in its entirety, enable the toothbrush to turn on only in response to determining that the brush head is inside a user's mouth. Other electric oral care appliances, however, still have various additional drawbacks. For example, due to the large amplitude of the brush head needed for an effective teeth cleaning, a user may experience unwanted and unpleasant splatter of toothpaste, water, and/or saliva prior to insertion of the brush head into the user's mouth, or in response to removing the brush head from the user's mouth while the power is still on. This may be extremely detracting from the user's overall experience. Furthermore, in current fast paced consumer markets, users have minimal amount of time and patience, and any negative aspect associated with a particular oral care appliance (e.g., splatter, restarting brushing due to excessive foam accumulation in the user's mouth), may turn the user off to that particular electric care appliance.

SUMMARY OF THE INVENTION

Accordingly, it is an objective of this invention to provide an oral care appliance, such as an electric toothbrush, that enables a more efficient and effective user experience while minimizing adverse features such as unwanted splatter of toothpaste, water, and saliva. This objective is achieved according to the present invention by providing a resonant system that utilizes non-linear properties to modify an amplitude of a brush head of an oral care appliance depending on whether the brush head is located inside a user's mouth, or if it is located outside of the user's mouth.

In a first exemplary embodiment, an oral care appliance utilizing non-linear resonant systems is provided. The oral care appliance includes a longitudinal shaft, a brush head located at a first end of the longitudinal shaft, and a handle located at a second end of the longitudinal shaft. The handle includes a motor operating at a substantially constant frequency and a substantially constant voltage. The motor is operative to generate a first amplitude for the brush head in response to the brush head being outside of a user's mouth. The motor is further operative to cause a second amplitude to be generated for the brush head in response to the brush head changing from being outside of the user's mouth to being inside of the user's mouth, where the second amplitude is greater than the first amplitude.

In a second exemplary embodiment, a method for increasing an amplitude of a brush head of an oral care appliance is provided. The method includes generating a first amplitude for the brush head in response to the brush head being outside of the user's mouth. The method also includes the brush head moving from being outside of the user's mouth to being inside of the user's mouth. The method then includes causing a second amplitude to be generated for the brush head in response to the brush head moving from being outside of the user's mouth to being inside of the user's mouth, where the second amplitude is greater than the first amplitude.

BRIEF DESCRIPTION OF THE DRAWINGS

The above and other features of the present invention, its nature and various advantages will be more apparent upon consideration of the following detailed description, taken in conjunction with the accompanying drawings in which:

FIG. 3 is another schematic illustration of a radial cross-section of an electric oral care appliance in accordance with various embodiments;

FIG. 4 is a schematic illustration of a longitudinal cross-section view of an electric oral care appliance in accordance with various embodiments;

DETAILED DESCRIPTION OF EXEMPLARY EMBODIMENTS

The present invention may take form in various components and arrangements of components, and in various techniques, methods, or procedures and arrangements of steps. The referenced drawings are only for the purpose of illustrated embodiments, and are not to be construed as limiting the present invention. Various inventive features are described below that can each be used independently of one another or in combination with other features. Furthermore, as used herein, the singular form of "a", "an", and "the" include plural references unless the context clearly dictates otherwise.

The described concept provides an electric oral care appliance having an actuator system for moving a brush head of the oral care appliance that, as described in detail herein, causes the brush head to move with a first amplitude when the brush head is in an unloaded state (e.g., out of the user's mouth), and a second amplitude, different than and greater than the first amplitude, when the brush head is in a loaded state (e.g., in the user's mouth tissue and fluid add mass to the brush head during brushing). This configuration is advantageous in that, according to an aspect of the described concept, the actuator system is described and configured such that the first amplitude is small enough that undesirable splatter of toothpaste, saliva, etc., will not occur when the brush head is in the unloaded state and moving with the first amplitude, and such that the second amplitude is large enough to provide sufficient brushing efficacy when the brush head is in the loaded state and moving with the second amplitude.

Figure 1A:
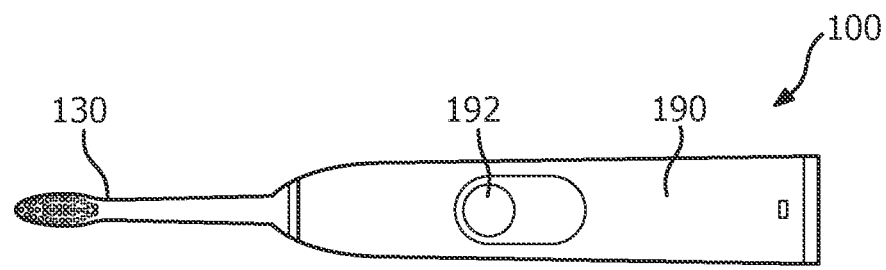
FIGS. 1A-C are schematic illustrations of an electric oral care appliance in accordance with various embodiments.
Figure 1B:
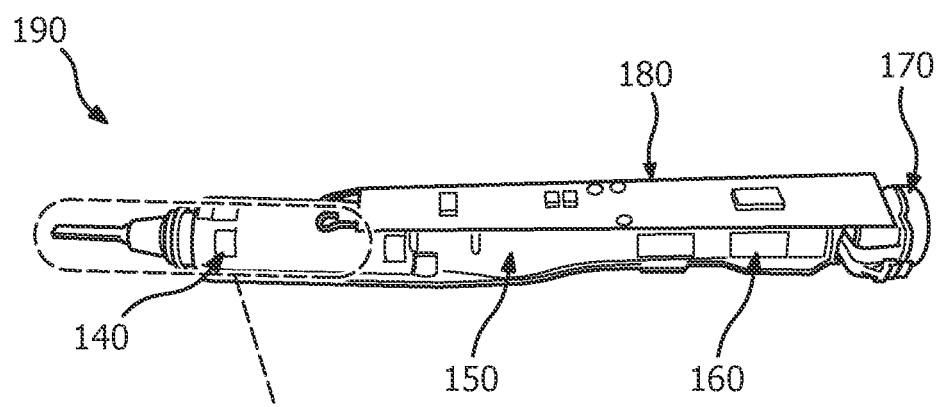
Figure 1C:
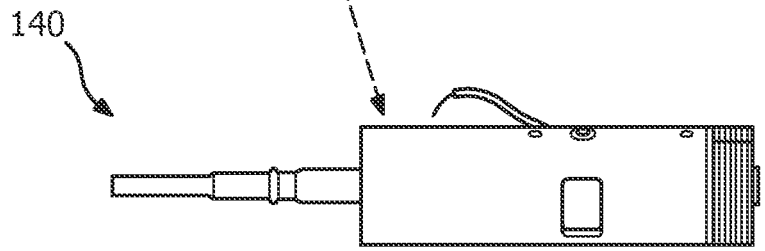

FIGS. 1A-C are schematic illustrations of an electric oral care appliance 100 in accordance with one non-limiting exemplary embodiment. In one non-limiting illustrated embodiment, oral care appliance 100 includes a handle portion 190, which is substantially annular, that is connected at a first end of handle portion 190 to a brush head 130. Within handle 190 is a motor or actuator 140 located proximate the first end of handle portion 190, as well as a battery 150 and a charging coil 160 located at a second end of handle portion 190 opposite the first end. Motor 140, battery 160, and charging coil 170 are housed within an annular frame 150. Frame 150 provides support within handle portion 190 so that components located therein, such as motor 140, battery 160, and charging coil 170 are substantially fixed in place and do not move while oral care appliance 100 is in operation. Handle portion 190 also includes an electronics board 180 which includes various electrical components and circuitry for oral care appliance 100. For example, handle 190, in one embodiment, includes an on/off button 192. When a user presses button 192, a button member on electronics board 180 may form an electrical path so that charge from battery 160 can flow to motor 140 to power oral care appliance 190 through electronics board 180. In one embodiment, charging coil 170 is used to charge battery 160, however persons of ordinary skill in the art will recognize that charging coil 170 may also be used to power motor 140 and/or electronics board 180. In one embodiment, button 192 is not included on handle 190, and oral care appliance 100 may turn on and/or off based on whether oral care appliance 100 is located within a user's mouth or outside of a user's mouth.

Figure 2:
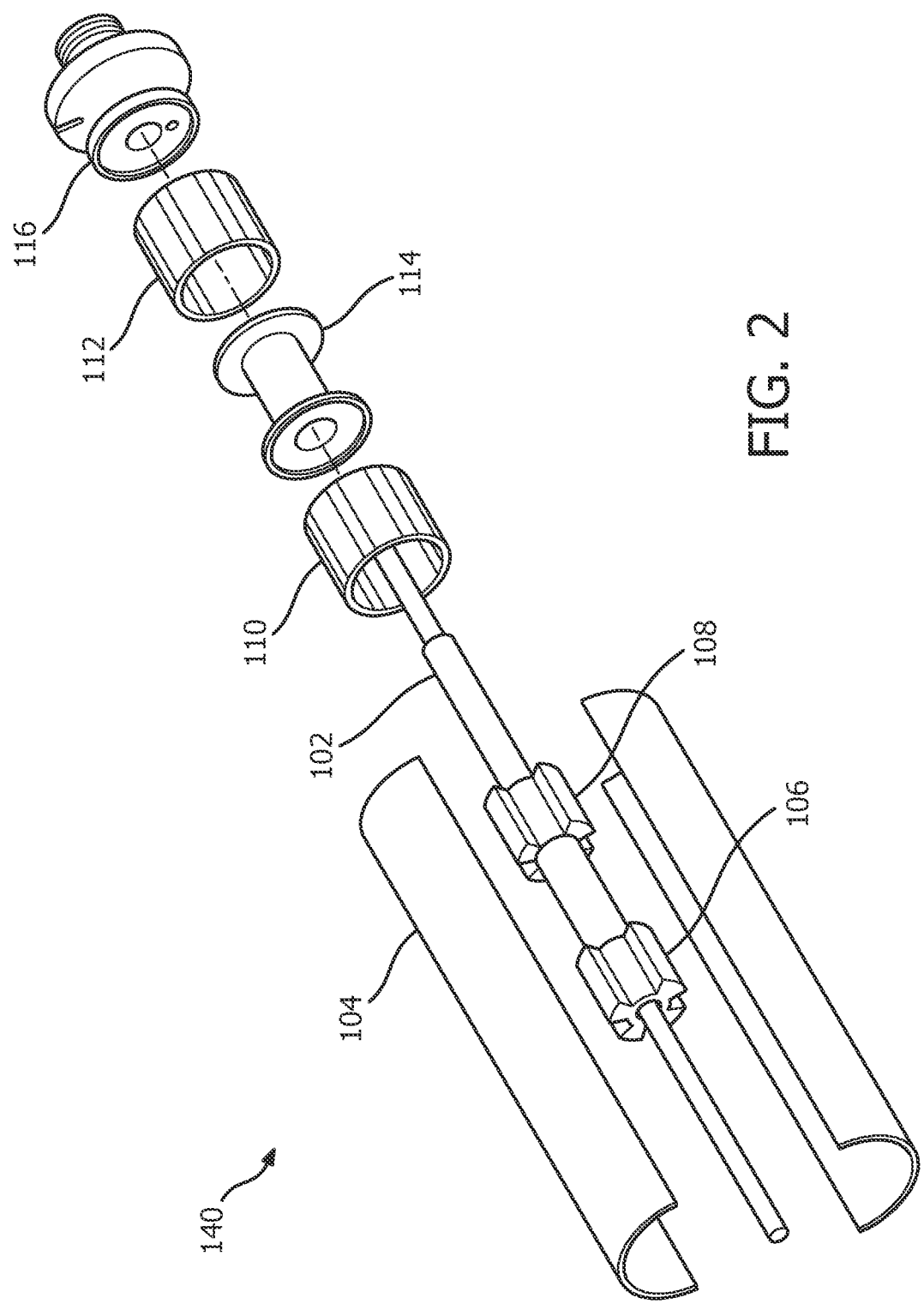
FIG. 2 is another schematic illustration of the electric oral care appliance of FIG. 1 and its components in accordance with various embodiment.

FIG. 2 is an exploded view of motor 140 showing various components thereof, and FIGS. 3 and 4 are two different schematic cross-sectional views of motor 140 illustrating particular components housed in motor 140. Oral care appliance 100, and in particular motor 140, includes a longitudinal shaft 102, which has a brush head 130 located at a first end, and a handle 140 located at a second end. Shaft 102 runs along a central axis of oral care appliance 100. In some embodiments, shaft 102 includes a spindle or itself is a spindle.

In one embodiment, brush head 130 has a plurality of bristles located on a first side of the brush head. Persons of ordinary skill in the art will recognize that although brush head 130 is described including a plurality of bristles, any suitable attachment may be used instead. For example, a tongue cleaner or a floss head may be attached to an attachment area located on at the first end of shaft 102. Motor 140 houses various components of oral care appliance 100, such as the motor or actuator described in detail herein. In the exemplary embodiment, handle 140 includes an elongated cylindrical case 104 having a high magnetic permeability. Case 104 is bounded at each end by a respective end cap 104a, 104b.

Within case 104 are two permanent magnetic assemblies 110 and 112, and a coil 114 located between the two magnetic assemblies 110, 112. Magnetic assemblies 110 and 112 have a number of alternating polarity magnets (labelled 111a and 111b, see FIG. 3) arranged circumferentially (e.g., north/south), with a magnetic spacer located between each different magnet 111a, 111b. In one embodiment, magnetic assembly 110 is aligned with magnetic assembly 112 such that magnets 111a, 111b of opposite polarities align with one another. Any number of magnets 111a, 111b may be used for each of magnetic assemblies 110 and 112. For example, in one particular embodiment, eight (8) magnets 111a, 111b may be used for each of assemblies 110 and 112, with four (4) north magnets 111a and four (4) south magnets 111b alternating between one another. In one particular embodiment, the number of magnets 111a, 111b used for each of magnetic assemblies 110 and 112 is an even number of magnets.

Motor 140 also houses two magnetic pole assemblies 106 and 108, which are positioned substantially within a volume encompassed by magnetic assemblies 110 and 112. Magnetic pole assemblies 106 and 108 each include a plurality of pole members 106a-106d evenly spaced around a ring portion adjacent to shaft 102. Any number of pole members 106a-106d may be used, for example, four, eight, sixteen, etc. (with four being shown in the exemplary embodiment of FIGS. 1-4). The magnetic pole assemblies 106 and 108 and shaft 102 typically are made of a magnetic material (e.g., iron), however other materials, such as ferromagnetic materials or insulating materials with a magnetic coating may also be used in certain embodiments.

In the illustrated exemplary embodiment, an end member 116 is included at the end of shaft 102. In one embodiment, end member 116 houses a bearing, where the bearing has a substantially small clearance between itself and shaft 102, thereby minimizing any debris that can enter motor 140. In another embodiment, however, debris is prevented from entering motor 140 by an additional housing surrounding and sealing motor 140. End member 116 may also "close" case 104 that foreign agents (e.g., dirt, water) do not enter into motor 140. In some embodiments, end member 116 is screwable onto an end of motor 140.

As mentioned previously, in a first exemplary embodiment, motor 140 includes four magnets 111a and four magnets 111b, which alternate circumferentially along an inner surface 105 of case 104. In some embodiments, between each of magnets 111a and 111b is a magnetic spacer 113, and the eight magnetic spacers 113 are at eight evenly spaced positions about casing 104, with one of magnets 111a and 111b located on either side of the spacer 113 in an alternating polarity arrangement. In one embodiment, magnetic spacer 113 is an empty space (e.g., air) between each of magnetics 111a and 111b. However, persons of ordinary skill in the art will recognize that any material may be used for magnetic spacer 113 such that a substantially lower magnetic field is present between each of magnets 111a and 111b. For example, magnetic space 113 may be an empty space or it may be an insulating material, a non-conductive material, or a material with a low magnetic permeability.

In the exemplary embodiment, magnetic pole assembly 106 includes four magnetic rotary pole assemblies 106a-d. Each pole member 106a-d is evenly spaced about a ring 107 adjacent to shaft 102. Persons of ordinary skill in the art will recognize that the number of poles may vary for different pole assemblies, and the use of four poles is merely exemplary. The pole members 106a-d are located at a first "cogging" position, which may be one of eight different preferred cogging positions. At an end of each pole member 106a-d, which extends radially outward from ring 107, is a closed magnetic flux loop 120. Flux loop 120 goes through the end of pole members 106a-d, magnets 111a, 111b, and case 104. The cogging effect delivers a spring function within a certain amount of degree rotations, such as fifteen degrees (15-degrees), and the restoring force of the spring function to the preferred cogging position decreases with the angle increment. However, the amount of degree rotations may depend on design, and the aforementioned is merely exemplary. Pole assembly 108 has a structure similar to pole assembly 106 just described, thus includes pole members of its own.

In response to a current being sent through coil 114, a magnetic field is generated inside case 104. As the current runs through coil 114, a magnetic pole is formed within magnetic pole assembly 106, and an opposite magnetic pole is formed within magnetic pole assembly 108. The polarity (e.g., north, south) of each magnetic pole assembly is dependent on the direction of the current flowing through coil 114. In this exemplary embodiment, the magnetic field formed by coil 114 goes clockwise in the upper black dotted loop and counter-clockwise in the lower black dotted loops, or vice versa. The arrangement of magnetic assemblies 110 and 112 is such that both attractive and repulsive forces will push shaft 102 in the same direction, and a closed magnetic loop is formed through the corresponding magnetic assemblies 110, 112, pole assemblies 106, 108, case 104, and shaft 102, as illustrated by the black loops in FIG. 4. In the exemplary embodiment, the material used for case 104 and pole assemblies 106 and 108 has a very high magnetic permeability. The higher the magnetic permeability, the large the motor constant will be, but the lower the stiffness of the actuator. The stiffness of the actuator increases by increasing the number of poles of pole assemblies 106, 108 and/or the number of permanent magnetic assemblies 110, 112.

As the alternating current flows through coil 114, an alternating magnetic field through pole assemblies 106, 108, shaft 102, magnetic assemblies 110, 112, and case 104 is produced. Magnetic assemblies 110, 112 lined with magnets 110 and 112 will act to repel or attract pole members 106a-106d of pole assemblies 106 and 108, depending on the position of the pole members 106a-d relative to magnets 111a, 111b and the polarity of pole members 106a-106d. This alternating field and attracting/repelling of pole members 106a-106d will cause shaft 102 to oscillate periodically to a desired amplitude.

Figure 5:
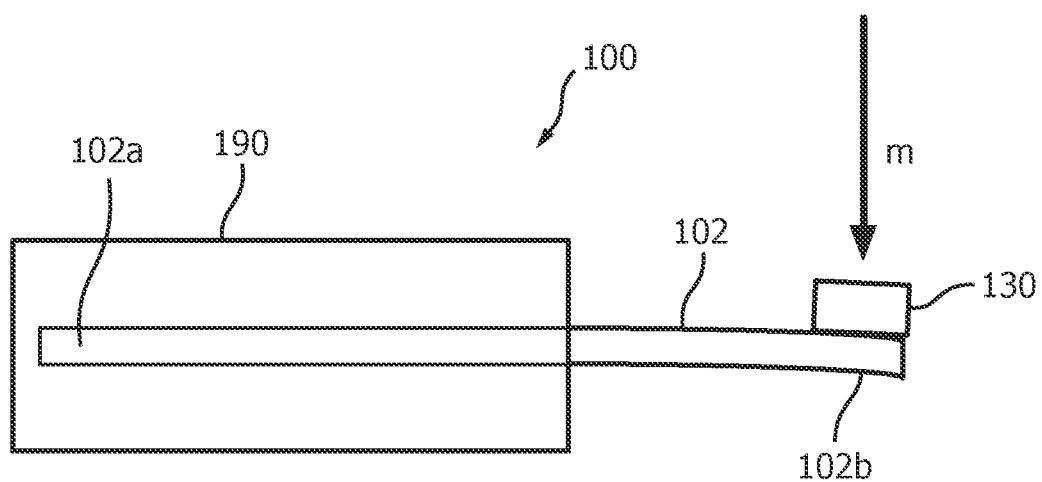
FIG. 5 is a schematic illustration of longitudinal cross-section view of an electric oral care appliance having mass applied to a brush head in accordance with various embodiments.

FIG. 5 is a schematic illustration of a longitudinal cross-sectional view of electric oral care appliance 100 with mass m applied to brush head 130 in accordance with various embodiments. Mass m corresponds to a mass applied to brush head 130 when pressed against a user's teeth while in a user's mouth. For example, mass m may correspond additional mass felt by brush head 130 in response to one or more of toothpaste, water, and/or saliva being applied to brush head 130. As mass is applied to brush head 130, the amplitude of brush head 130 will increase. The amplitude of brush head 130 and the rotation angle of pole assemblies 106 and 108 are substantially the same, so when the amplitude of brush head 130 increase, the rotational angle of pole assemblies 106 and 108 also increases because of the increase of rotational inertia. After the mass is removed, the amplitude of brush head 130 will decrease, and the angle of pole assemblies 106 and 108 will also decrease because the reduction in rotational inertia due to the effective magnetic spring constant increasing.

Figure 6:
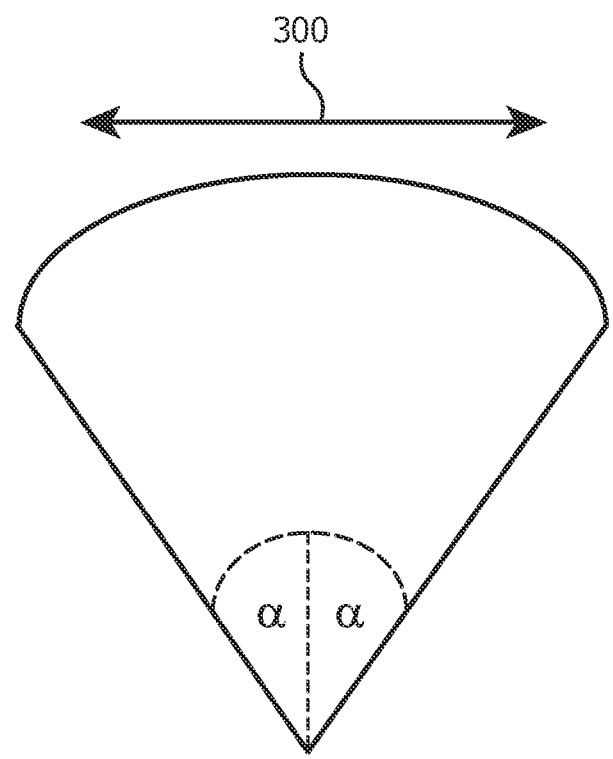
FIG. 6 is a perspectives of an amplitude of a brush head for an electric oral care appliance moving with an oscillatory, rotational motion in accordance with various embodiments.

FIG. 6 schematically illustrates an amplitude of brush head 130 of electric oral care appliance 100 moving in a rotational direction as it rotates about a fixed rotational axis in accordance with the illustrated exemplary embodiment. For example, as a square wave energizing signal is inputted through the actuator of electric oral care appliance 100 just described, magnetic assemblies 110 and 112 cause shaft 102 to rotate about the longitudinal axis of shaft 102 a first direction (e.g., clockwise) during a first portion of the square energizing signal, and in a second direction (e.g., counter-clockwise) during a second portion of the square energizing signal.

As brush head 130 moves from the first direction to the second direction, the translational motion of brush head 130 may be described by a line 300, which represents the path of brush head 130 as it rotates to a first position and then rotates to a second position. When rotating to the first position, brush head 130 moves from a "zero" position, or center position, to the first position via a rotation by an angle α. In some embodiments, the zero position corresponds to one of the preferred cogging positions. Brush head 130, in response to the square energizing wave going from a first portion to zero, then rotates in the second direction by an angle of a to return to the zero position. As the square energizing wave moves to the second portion, brush head 130 rotates in the second direction further by an angle α. After the second portion of the square energizing wave, the wave returns to zero, causing brush head 130 to once again rotate by an angle α in the first direction to return to the zero position. This process may repeat throughout the course of the operation of oral care appliance 100, carving out the path of motion of brush head 130.

The angle α that brush head 130 rotates, in some embodiments, is described as half of the amplitude of brush head 130. For example, if an amplitude is 10-degrees, this would correspond to a being 5-degrees so that brush head 130 would oscillate clockwise 5-degrees from its "zero"-position, as well as rotate counter-clockwise 5-degrees from the "zero" position. In one particular embodiment, brush head 130 has an amplitude between 5 and 10-degrees, or a between 2.5 and 5-degrees. In another particular embodiment, brush head 130 has an amplitude between 10 and 20-degrees, or α between 5 and 10-degrees. However, persons of ordinary skill in the art will recognize that any amplitude may be used, and the amplitude may be based on any number of factors (e.g., the number of cogging positions).

As noted elsewhere herein, in some embodiments, the amplitude of brush head 130 depends on various conditions for oral care appliance 100 and/or brush head 130 itself. For example, and according to an aspect of the described concept, oral care appliance 100 is structured and configured such that brush head 130, when located inside a user's mouth, will have a higher amplitude than when located outside of a user's mouth. This may be extremely beneficial for users as they may have decreased amounts of splatter due to toothpaste, water, and/or saliva when brush head 130 is outside of the user's mouth.

In one exemplary embodiment, oral care appliance 100 has a first amplitude when it is in an unloaded state (e.g., out-of-mouth). For example, in the unloaded state, oral care appliance 100 has a substantially small amplitude. By having a substantially small amplitude, oral care appliance 100 may reduce any extraneous splatter that may occur by oral care appliance 100 being "on" but not actively used to brush. In a particular embodiment, the first amplitude in the unloaded state corresponds to an amplitude less than 10-degrees, or an angle α less than 5 degrees, however persons of ordinary skill in the art will recognize that this is merely exemplary. The first amplitude corresponds to any amplitude that is small enough such that minimal splatter may occur. For example, the first amplitude in the unloaded state may be 4-degrees, or α being 2-degrees), which may be small enough to allow minimal splatter, but large enough so that a user recognizes that the oral care appliance is on.

In some embodiments, oral care appliance 100 has a second amplitude when it is in a loaded state (e.g., in-mouth). For example, in the loaded state, oral care appliance 100 has a larger amplitude than the amplitude in the unloaded state. This may allow the user to have an effective brushing experience because the amplitude will be large enough to effectively clean the user's teeth, gums, etc. For example, the second amplitude may be between 9 and 12-degrees, or a between 4.5 and 6-degrees. As another example, the second amplitude may be between 10 and 20-degrees, or a between 5 and 10-degrees. Persons of ordinary skill in the art will recognize, however, than any amplitude value, or any α value, may be used, and the aforementioned are merely exemplary. The ratio of the amplitudes of the loaded to unloaded states includes, but is not limited to, approximately 2:1, 3:1, 3:2, 4:1, so long as an effective difference between the out of mouth amplitude and the in-mouth amplitude is experienced by the user.

Persons of ordinary skill in the art will recognize that although only two amplitudes are described for two states, any number of amplitudes corresponding to any number of states may be used. For example, the unloaded state may have two different levels depending on whether or not oral care appliance 100 is on with no toothpaste or water, or if oral care appliance 100 is on with toothpaste or water.

In one embodiment, oral care appliance 100 automatically changes from the first amplitude to the second amplitude as a result of a change in the moment of inertia of oral care appliance 100 based on whether it is out of the user's mouth or if it is inside of the user's mouth. For example, when oral care appliance 100 is out of the user's mouth, oral care appliance 100 has a first moment of inertia. When oral care appliance 100 is inside the user's mouth, water, saliva, the user's gums, toothpaste, the user's cheek, oral mucosa, and mouth soft tissue may cause oral care appliance 100 to have a second moment of inertia, which causes oral care appliance 100 to automatically change from having a first amplitude to a second amplitude.

Figure 7:
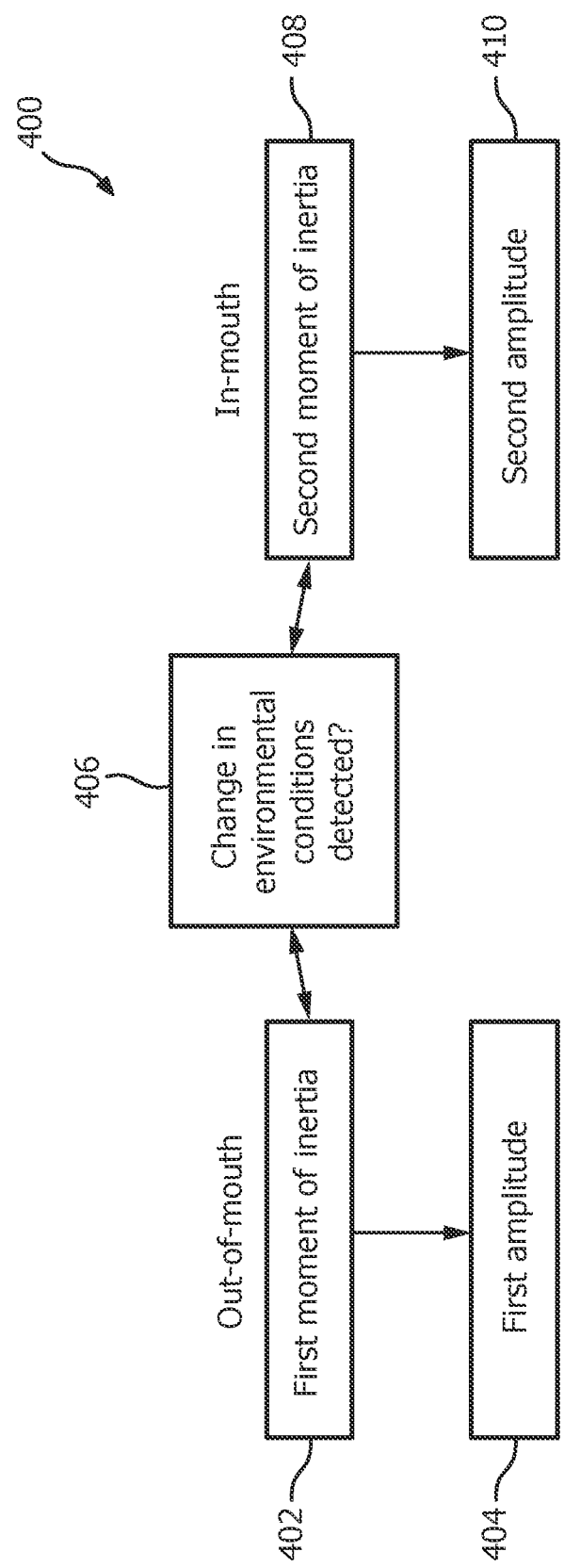
FIG. 7 is an illustrative flowchart of a process for generating various amplitudes for a brush head of an electric oral care appliance for both out of mouth and in-mouth states in accordance with various embodiments.

FIG. 7 is an illustrative flowchart of a process for generating various amplitudes for brush head 130 of the exemplary electric oral care appliance 100 for both out of mouth and in-mouth states in accordance with various embodiments. A process 400 may begin, in some embodiments, at a step 402. At step 402, a first moment of inertia is determined for electric oral care appliance 100. For example, oral care appliance 100 of FIG. 1, in an out-of-mouth environmental state, is characterized by a lack of water, teeth, gums, or other objects commonly associated with a user's mouth, being present on or near brush head 130, which causes oral care appliance 100 to have a first moment of inertia.

At step 404, a first amplitude is generated for brush head 130 of the oral care appliance 100 as a result of and based on the first moment of inertia 402. For example, the first moment of inertia 402 may correspond to oral care appliance 100 being outside of a user's mouth as just described. In this scenario, brush head 130 of oral care appliance 100 has a first amplitude 404 that corresponds to the first moment of inertia 402. At step 406, a change in environmental conditions is experienced by oral care appliance 100 which, in turn, causes oral care appliance 100 to have a second moment of inertia. For example, a change of brush head 130 from being outside a user's mouth to inside the user's mouth may correspond to a change in the environmental state of oral care appliance 100.

At step 408, a second moment of inertia is determined for oral care appliance 100. In some embodiments, the second moment of inertia corresponds to oral care appliance 100 being in a user's mouth and thus interacting with a user's teeth, gums, water, toothpaste, the user's cheek, oral mucosa, mouth soft tissue, and/or saliva. In some embodiments, the second moment of inertia 408 is determined based on and as a result of environmental state changes shown at step 406. For example, when oral care appliance 100 is placed inside the user's mouth, the user's teeth, gums, water, toothpaste, the user's cheek, oral mucosa, mouth soft tissue, and/or saliva may act as if there is a mass added to brush head 130. The additional mass on brush head 130 alters the moment of inertia of oral care appliance 100 from the first moment of inertia 402 to the second moment of inertia 408.

At step 410, a second amplitude is automatically generated by oral care appliance 100 for brush head 130 as a result of and based on the second moment of inertia 408. For example, in response to additional mass (e.g., saliva, water, etc.) being on brush head 130, and therefore a change in the moment of inertia of oral care appliance 100—occurring, the amplitude of brush head 130 changes. In some embodiments, the amplitude increases in response to the change from the first moment of inertia to the second moment of inertia. For example, if first amplitude is 4-degrees, or a equal to 2-degrees, the second amplitude may be between 9 and 12-degrees (α between 4.5 and 6-degrees).

In some embodiments, process 400 may instead begin at step 408, so that oral care appliance 100 initially has the second moment of inertia 408 (e.g., corresponding to brush head 130 being in the user's mouth) and therefore having the second amplitude 410. In response to a change in environmental conditions 406 (e.g., removing brush head 130 from the user's mouth), the moment of inertia for oral care appliance 100 changes from the second moment of inertia 408 to the first moment of inertia 402. Accordingly, the amplitude of brush head 130 will also change from the second amplitude 410 to the first amplitude 404. For example, while in the user's mouth, oral care appliance 100 operates with an amplitude between 9 and 12-degrees, or a between 4.5 and 6-degrees, however, after brush head 130 has been removed from the user's mouth, the amplitude will decrease to 4-degrees, or a being 2-degrees. Any extraneous splatter will be reduced because the amplitude of brush head 130 decreases based on the change of oral care appliance 100 from being inside the user's mouth to being outside the user's mouth.

The moment of inertia for an object, such as oral care appliance 100 as just described, is defined by the ratio between the system's angular moment and the system's angular velocity about an axis. The moment of inertia for a continuous system may be defined by Equation 1:

$$I = \int \rho(r) r^2 dV \qquad \text{Equation 1.}$$

In Equation 1, the moment of inertia, I, is found by integrating the density ρ(r) of an object over the volume of the object. As shown in Equation 1, the moment of inertia is related to the density of the object. For example, a solid rod with a uniform mass distribution will have a first moment of inertia, however the same solid rod having a uniform mass distribution except at one end where an additional mass is located, will have a second moment of inertia which is greater than the first due to the additional mass.

Figure 8:
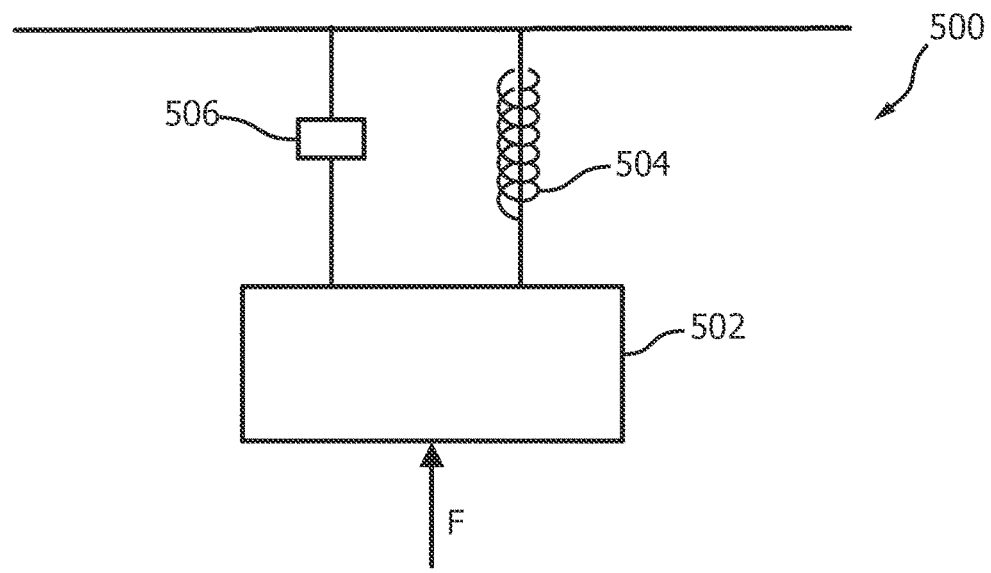
FIG. 8 is a schematic illustration of a damped, driven, harmonic oscillator in accordance with various embodiments.

FIG. 8 is a schematic illustration of a damped, driven, harmonic oscillator system in accordance with various embodiments. A system 500 includes a mass 502 coupled to a spring 504, and to a damping source 506. One end of spring 504 and damping source 506 is coupled directly to mass 502, whereas the other end of spring 504 and damping source 506 is coupled to a fixed surface, such as a wall. System 500 has a force, F, that drives the mass towards the wall such that spring 504 compresses when the driving force is applied in a positive direction. Force F will also drive the mass away from the wall, extending spring 504 when the driving force is in the negative direction.

In some embodiments, the driving force F may be sinusoidal in time, t, and may be expressed as $F(t) = F_0 \cos(\omega t - \psi)$, where $F_0$ corresponds to a magnitude of the driving force, ω corresponds to a driving frequency, and ψ corresponds to a driving phase. In this scenario, the equation of motion for system 500 is described by:

$$m \frac{d^2 x}{dt^2} + c \frac{dx}{dt} + kx = F_0 \cos(\omega t - \psi). \qquad \text{Equation 2}$$

In Equation 2, m corresponds to mass 502, c corresponds to the damping 506, k corresponds to a spring constant of spring 504, and $$\frac{d^2 x}{dt^2} \text{ and } \frac{dx}{dt}$$

correspond to the second and first derivatives, respectively, of the position of mass 502 with respect to time. In some embodiments, the natural frequency of system 500, $\omega_0$, may be described by $$\omega_0 = \sqrt{\frac{k}{m}},$$

and the damping ratio, β, may correspond to $$\beta = \frac{c}{2\sqrt{mk}}.$$

Using these expressions for $\omega_0$ and β, Equation 2 may be rewritten as:

$$\frac{d^2 x}{dt^2} + 2\beta \omega_0 \frac{dx}{dt} + \omega_0^2 x = \frac{F_0}{m} \cos(\omega t - \psi). \qquad \text{Equation 3}$$

The steady state solution to Equation 3, where r corresponds to the ratio of the driving frequency to the natural frequency, is $$x = \frac{\frac{F_0}{m}}{\omega_0^2} A(r, \beta) \cos(\omega t - \psi - \theta),$$

where $$A(r, \beta) = \frac{1}{\sqrt{(1 - r^2)^2 + (2\beta r)^2}},$$

and $\theta = \tan^{-1}[2\beta r / 1 - r^1]$. Thus, the amplitude of the mass will be described by:

$$\text{Amplitude} = \frac{\frac{F_0}{m}}{\omega_0^2} A(r, \beta).\qquad \text{Equation 4}$$

Figure 9:
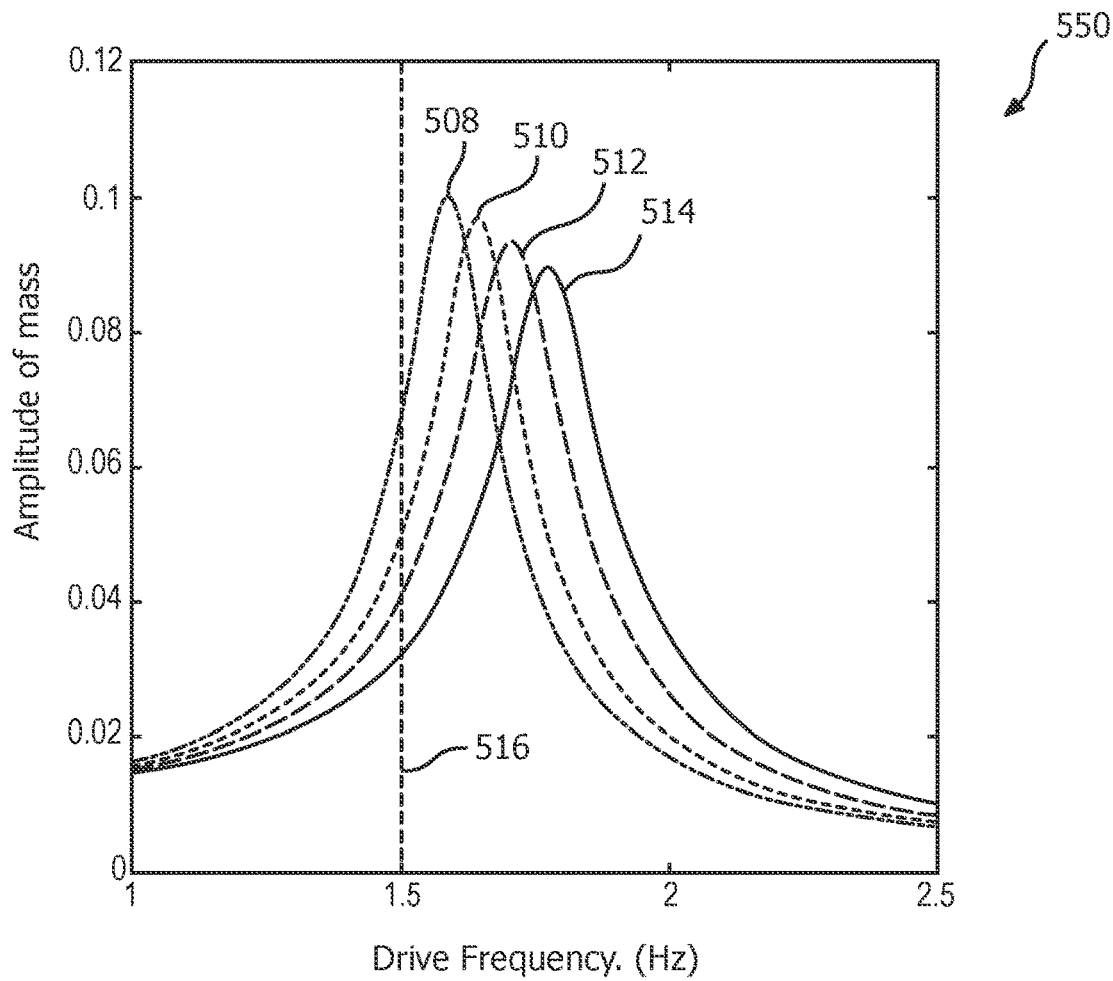
FIG. 9 is an illustrative graph of amplitude versus frequency for various masses in linear systems in accordance with various embodiments.

FIG. 9 is an illustrative graph of amplitude versus frequency for various masses for linear systems in accordance with various embodiments. A graph 550 describes an amplitude of a steady state solution for a linear system, such as damped driven harmonic oscillator 500 of FIG. 9, in relation to the system's driving frequency for various masses. Graph 550 represent the amplitude and frequency relationship for various masses, with a line 508 representing a first mass, a line 510 representing a second mass, a line 512 representing a third mass, and a line 514 representing a fourth mass. For the relationship described by Equation 4, the first mass is greater than the second mass, which is greater than the third mass, which is greater than the fourth mass. For a particular operating frequency, such as 1.5 Hz, represented by a line 516, as mass increases with all other parameters remaining constant, the amplitude of the system also increases.

Figure 10:
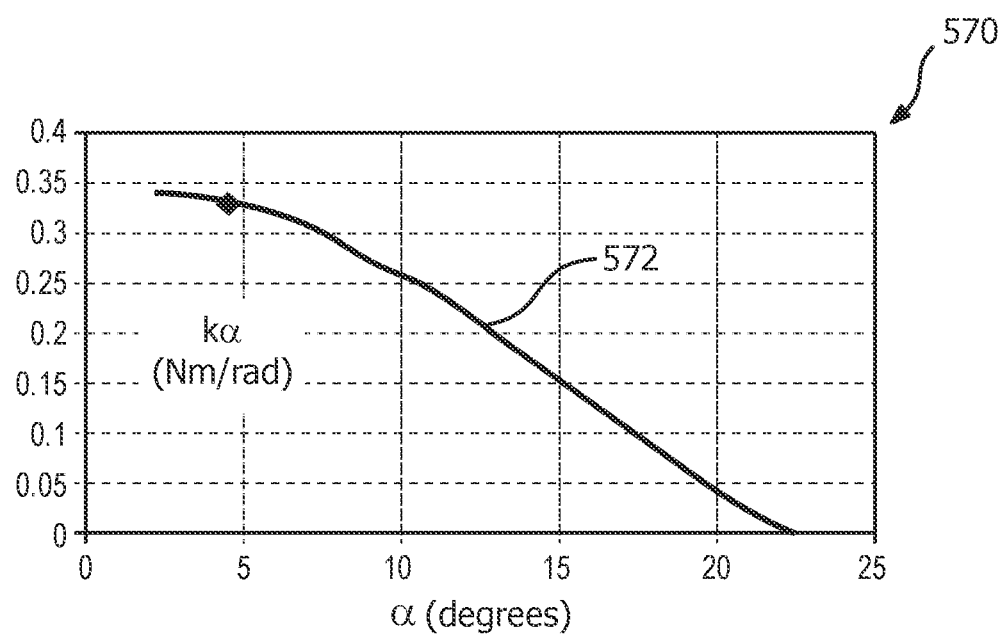
FIG. 10 is an illustrative graph of a non-linear spring rate in terms of rotation angle in accordance with various embodiments.

FIG. 10 is an illustrative graph of a non-linear spring rate in terms of rotation angle in accordance with various embodiments. A graph 570 describes a static magnetic spring rate, where the spring rate decreases as the rotation angle increases, as shown by a line 572. When brush head 130 of oral car appliance 100 has no mass applied to it, brush head 130 oscillate back and forth at a first amplitude (e.g., unloaded state). The first amplitude of brush head 130 of oral care appliance 100 corresponds to an angle of rotation of pole members 106a-106d about shaft 102. When the angle of rotation of pole members 106a-106d is small, the effective magnetic spring rate of toothbrush 100 is large. As mass is applied to brush head 130 of oral care appliance 100 when the operating frequency of oral care appliance 100 is below the frequency where peak amplitude occurs in the unloaded state, the amplitude of brush head 130, and thus the angle of pole members 106a-d, increases. The increased inertia and lower effective spring rate causes the frequency at which the peak amplitude occurs to decrease and, if the operating frequency is below the peak amplitude frequency in the initial moment of inertia state, allows the amplitude of brush head 130 of oral care appliance 100 to increase as the peak amplitude frequency approaches the operating frequency. As shown by graph 570, as the rotation angle of pole members 106a-106d increase, the spring rate of oral care appliance 100 will correspondingly decrease, which will allow oral care appliance 100 to have a larger amplitude when it is in the loaded state (e.g., in the user's mouth) as opposed to a small amplitude when it is in the unloaded state (e.g., outside the user's mouth).

Figure 11:
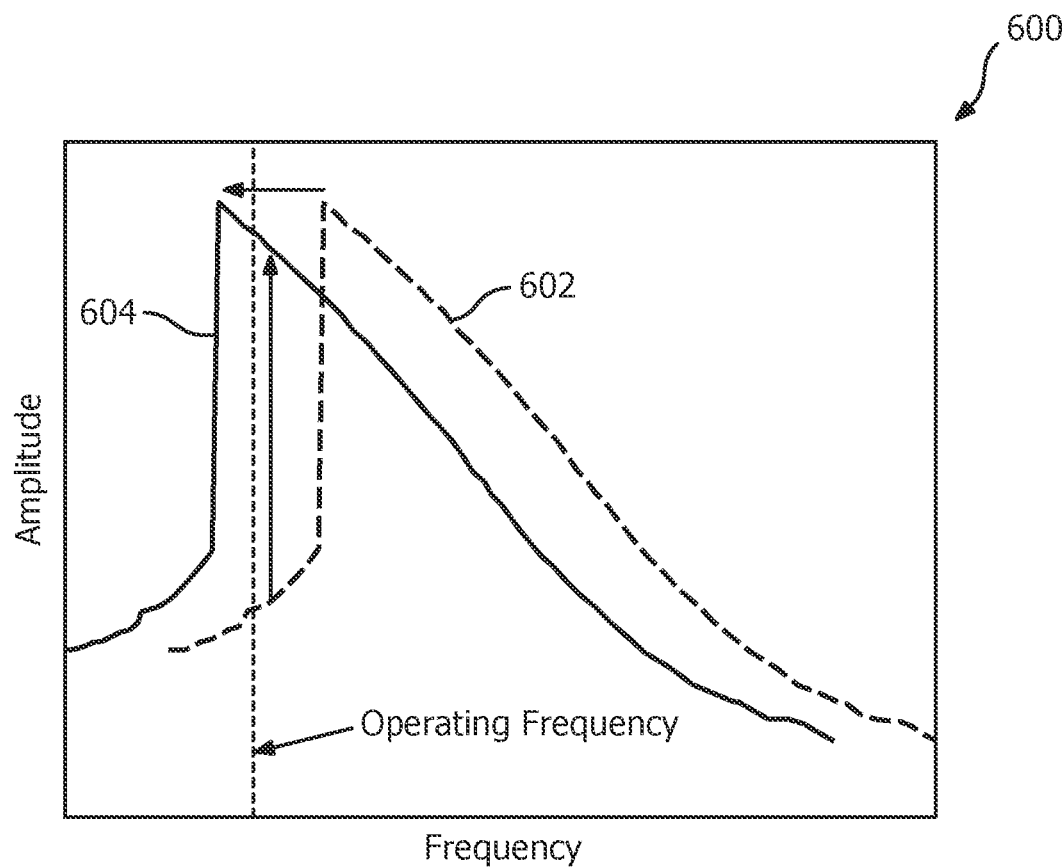
FIGS. 11 and 12 are an illustrate graph of amplitude versus frequency for a non-linear system in accordance with various embodiments.
Figure 12:
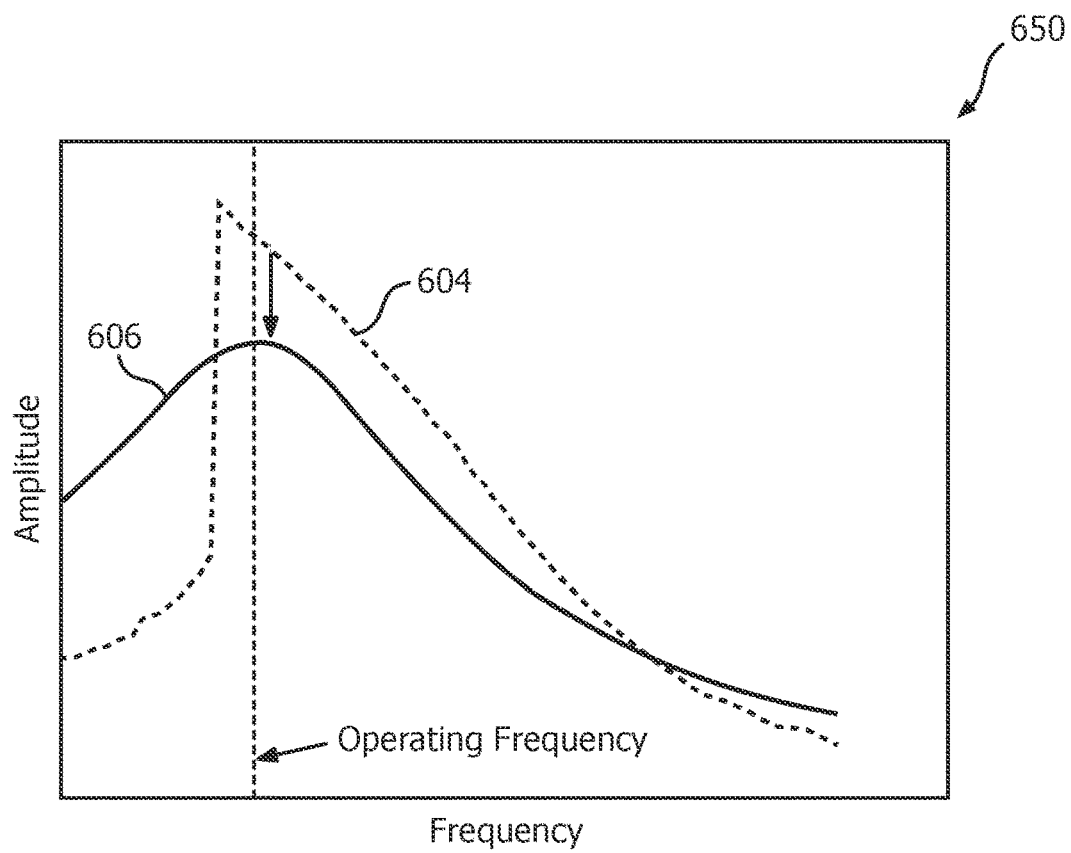

FIGS. 11 and 12 are illustrative graphs of amplitude versus frequency for non-linear systems in accordance with various embodiments. In the non-limiting exemplary embodiment, the effective magnetic spring for electric oral care appliance 100 is non-linear. This is due, in part, to the rotation angle dependent stiffness, however factors such as the inverse relationship between the magnetic field strength and distance also contribute to the non-linear effective magnetic spring. The general equation of motion for the non-linear system is described by:

$$m\frac{d^2\theta(t)}{dt^2} + c\frac{d\theta(t)}{dt} + k(\theta)\theta(t) = f(t).\qquad \text{Equation 5}$$

In Equation 5, $\theta(t)$ is the rotation angle of a pole member (e.g., members 106a-d), m is the moment of inertia, c is damping, $k(\theta)$ is the stiffness of the system which is dependent on the rotation angle $\theta(t)$, and f(t) is the periodic excitation force. When electric oral care appliance 100 goes from being outside of the user's mouth to being inside of the user's mouth, the moment of inertia of brush head 130 increases, which shifts a first amplitude curve 602 of a graph 600 in a lower frequency direction. Thus, first amplitude curve 602 shifts to a second amplitude curve 604 of graph 600. As first amplitude curve 602 shifts to second amplitude curve 604, the non-linear jump point moves from being greater than the operating frequency to being equal to or less than the operating frequency. For example, the non-linear jump point of first amplitude curve 602 is to the right of the operating frequency of FIG. 11, whereas the non-linear jump point of second amplitude curve 604 is to the left of the operating frequency.

In addition to the increase in the moment of inertia of brush head 130, when inside the user's mouth, water, saliva, toothpaste, etc., act as a damping force on brush head 130. The effect of damping is seen in a graph 650 of FIG. 12. In the illustrated embodiment, second amplitude curve 604 is smoothed and the amplitude decreased due to damping effects, as seen by a third amplitude curve 606 of graph 650. Third amplitude curve 606 has a substantially similar non-linear jump point as second amplitude curve 604, however the peak amplitude of third amplitude curve 606 is less than the peak amplitude of second amplitude curve 604. Furthermore, the abrupt discontinuity at the non-linear jump point is smoothed due to the damping effects, leading to a smooth amplitude curve (e.g., third amplitude curve 606).

Figure 13:
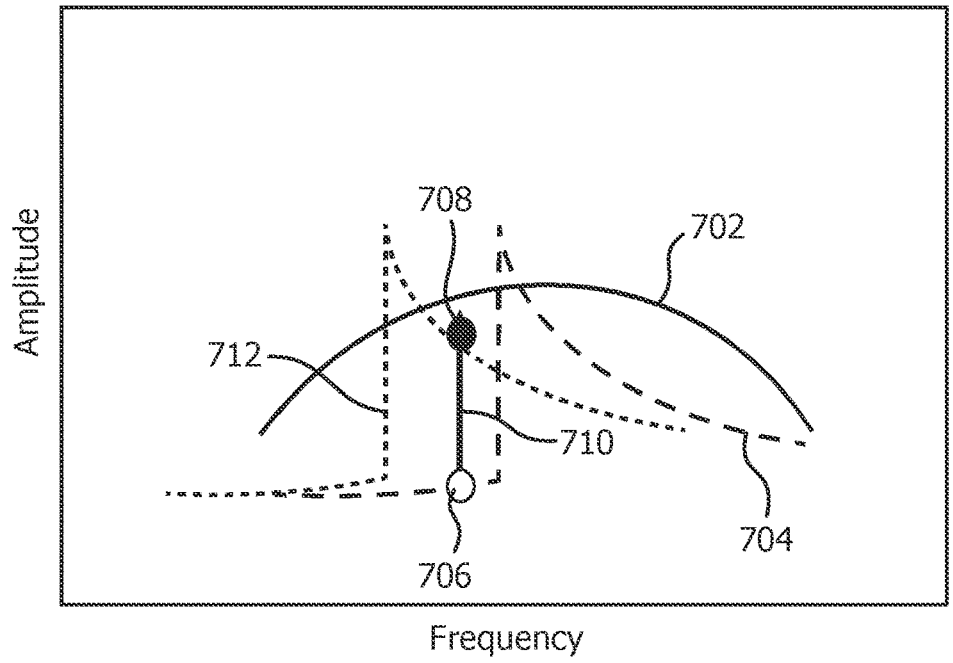
FIG. 13 is another illustrative graph of amplitude versus frequency for loaded and non-loaded states in accordance with various embodiments.

FIG. 13 is another illustrative graph of amplitude versus frequency for loaded and non-loaded states in accordance with various embodiments. A graph 700 corresponds to an amplitude versus frequency plot for loaded and unloaded states for a resonant system. A solid line 702 corresponds to a plot of amplitude versus frequency for a loaded state, whereas a dashed line 704 corresponds to a plot of amplitude versus frequency for an unloaded state. A dotted line 712 corresponds to line 704 after a mass has been applied to the brush head.

In an unloaded state, such as when no mass is applied to a brush head, the non-linear system may be described by line 704. As the applied mass increases, the amplitude of the unloaded state slightly increases until a critical point is reached when the non-linear jump point equals to the operating frequency, where the amplitude suddenly increases greatly. When a mass is applied to the brush head, line 704 shifts to the left, which is shown by line 712. If an operating frequency 706 for line 704 is kept fixed, as mass is applied to the brush head, the curve moves to the left such that the discontinuity point shifts from the right side of the operating frequency to being on the left side of the operating frequency, as shown by point 708. As described above, as the mass on the brush head increases, the amplitude of the system increases, which means that the angle of the pole assembly increases, which corresponds to the spring constant decreasing.

Line 702 corresponds to the damping effect felt by the brush head when it is placed inside the user's mouth. The user's teeth, gums, saliva, etc., damp down the brush head cause the amplitude of the system to decrease. This damping lowers the overall peak of curves 704 or 712.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

What is claimed is:

1. An oral care appliance, comprising:
    a longitudinal shaft;
    a head located at a first end of the longitudinal shaft; and
    a handle located at a second end of the longitudinal shaft opposite the first end, wherein the handle comprises a motor housed within the handle, the motor being operable fixed operating frequency in response to a constant non-linear energizing voltage signal, wherein:
    responsive to no mass being applied to the head, the head has a first moment of inertia and the motor generates a first amplitude of oscillatory rotational motion through a first amount of degree of rotations about a longitudinal axis of the longitudinal shaft for the head; and
    responsive to mass being applied to the head, the head has a second moment of inertia and the motor generates a second amplitude of oscillatory rotational motion through a second amount of degree of rotations about the longitudinal axis of the longitudinal shaft for the head, wherein the second amplitude is greater than the first amplitude;
    wherein the motor further comprises at least one set of permanent magnets located at a fixed position within the handle, the at least one set of permanent magnets alternating circumferentially between a first polarity and a second polarity.

2. The oral care appliance of claim 1, wherein, responsive to the head being pressed against one or more of teeth, gums, cheek, oral mucosa mouth soft tissue or saliva inside a user's mouth, mass is applied to the head such that the head has the second moment of inertia and the motor generates second amplitude for the head.

3. The oral care appliance of claim 2, further comprising:
    responsive to the head being removed to outside of the user's mouth and no mass is applied to the head, the head of the oral care appliance changes to the first moment of inertia and the motor generates the first amplitude for the head.

4. The oral care appliance of claim 1, wherein the ratio of the second amplitude to the first amplitude is at least 2:1.

5. The oral care appliance of claim 1, wherein:
    the first amplitude of oscillatory rotational motion through a first angle is 4-degrees; and
    the second amplitude oscillatory rotational motion through a second angle is between 9-degrees and 12-degrees.

6. The oral care appliance of claim 1, wherein the fixed operating frequency is a frequency value between 100 Hz and 350 Hz.

7. The oral care appliance of claim 1, wherein:
    the first amplitude of oscillatory rotational motion through a first angle is between 2-degrees and 8-degrees; and
    the second amplitude of oscillatory rotational motion through a second angle is between 9-degrees and 18-degrees.

8. The oral care appliance of claim 1, wherein
    a magnetic spacer is located between each magnet circumferentially; and
    magnets having opposing polarities align with one another from each of the at least one set of permanent magnets.

9. The oral care appliance of claim 8, wherein the motor further comprises:
    at least one set of rotary poles each being aligned with the corresponding at least one set of permanent magnets; wherein:
    each pole from the at least one set of rotary poles rotates by a first angle causing the head to have the first amplitude when no mass is applied to the head; and
    each pole from the at least one set of rotary poles rotates by a second angle causing the head to have the second amplitude when mass is applied to the head.

* * * * *